Dec. 25, 1962 R. O. RUBEL, JR Plant Pat. 2,206
CAMELLIA PLANT
Filed June 15, 1961
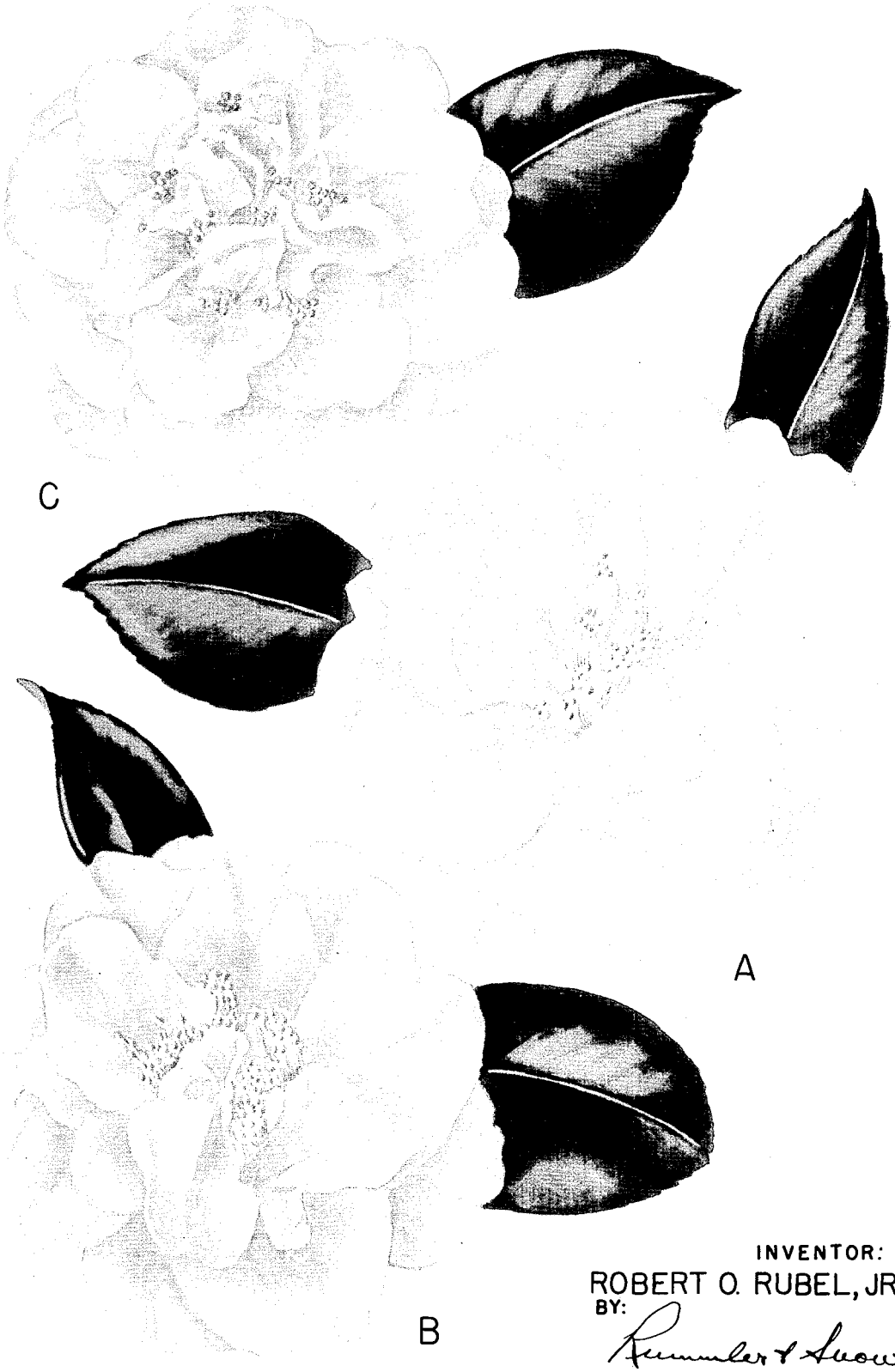
INVENTOR:
ROBERT O. RUBEL, JR.
BY:
Rummler & Snow
ATT'YS United States Patent Office Plant Pat. 2,206
Patented Dec. 25, 1962

2,206
CAMELLIA PLANT

Robert O. Rubel, Jr., Crichton Station, Ala., assignor to Cliff Harris, Mobile, Ala.

Filed June 15, 1961, Ser. No. 117,478
1 Claim. (Cl. 47—60)

This invention relates to camellia plants and particularly concerns a new and distinct variety of camellia plant discovered by me in my nursery at Mobile, Alabama. This new variety originated as a seedling of unknown parentage and is distinguished by its characteristic of producing several distinctively different blooms, simultaneously, of a generally dark salmon pink coloring. This new variety developed from a seed planted in 1932 and, having observed its consistency of blooming habit, I asexially propagated the new plant in 1939, by both cuttings and grafting at my nursery in Mobile, Alabama. Continued asexual propagation of the new variety, at my aforesaid nursery, through several successive generations and for more than ten years has demonstrated that the distinctive blooming habit of the plant holds true from generation to generation.

The accompanying full color drawings show typical full-blown blooms of my new variety and illustrate the three most predominate types of coloring occurring in the simultaneously produced flowers of the new plant. The bloom designated "A" in the drawings occurs most frequently and is particularly distinguished by its small irregular stripes of salmon pink coloring on a pinkish white background, the stripes running lengthwise of the petals rather than in the usual variegated pattern wherein the coloring is speckled, spotted or mottled. The blooms designated "B" and "C" also occur on the same plant and at the same time as the type "A" bloom, although in lesser numbers and the numerical proportions of "B" and "C" to "A" are not always the same from plant to plant or from season to season on the same plant. The bloom type designated "B" is a solid colored bloom with the petal coloring varying from dark to light salmon pink substantially as shown. The bloom type designated "C" is mainly white but with some of the same form and color of stripes as the type "A" bloom. All three types of blooms, however, are of the same incomplete double form and are of substantially the same size.

This new plant has a vigorous upright growth habit, with abundant foliage of a typical camellia type and color, and is extraordinarily winter hardy and resistant to repeated freezes. The asexually produced progeny of the original discovery have all held true to form for more than ten years and, in my nursery at Mobile, Alabama, have borne perfect blooms after each of more than 36 freezes with the temperature one year dropping to 17° F.

A detailed description of my variety of camellia plant is as follows (color designations are according to "A Dictionary of Color" by Maerz and Paul, except where terms of ordinary dictionary significance are employed):

*Plant*

Origin: Seedling of unknown parentage.
Classification: *Camellia japonica.*
Present method of propagation: Grafting and rooted cuttings.
Form: Compact bush.
Height: Average for camellia plants.
Growth: Vigorous, upright and branching. Growth is more rapid than usual for camellia plants.
Leaves:
*Quantity.*—Abundant.
*Size of leaf.*—Average, 4½ inches long x 2 inches wide.

*Shape of leaf.*—Ovate, edges serrated.
*Texture.*—Leathery and glossy. Leaf has prominent ribs and veins.
*Color.*—Same as usual camellia plants. Upper side—dark green. Under side—light green.
*Petioles.*—Length—¼ inch.

*Bud*

Size: Large. 1 3/16 inches long, 1 3/16 inch diameter.
Form: Elliptic-ovate. Opens slowly.
Color: Usual for most camellia buds. Medium green when sepals first divide; brownish green when sepals begin to unfurl.
Sepals: 8 to 9 in number. Upstanding. Partially hooded over bud.
Calyx: Broad. Smooth aspect. Does not split.
Peduncle: Not hairy.

*Flower*

Blooming habit: Recurrent. Blooms profusely from early fall until late March where commonly grown.
Size: Medium. Diameter, 4 to 6 inches. Depth, 3 to 3½ inches.
Borne: Singly.
Shape: High center.
Petalage:
*Number of petals.*—Approximately 24.
*Arrangement.*—Irregular. Incomplete double arrangement with 6 or 7 central petals standing higher than remainder.
*Shape.*—Obovate, crinkled and not serrated.
*Color.*—Type "A"—Light to dark salmon pink (Plate 1, I–1 to G–4) streaks or stripes, running lengthwise of petal, on pink tinted white (Plate 1, H–1) background. Same coloring on front and back sides of all petals. Type "B"—Solid pink color over all of petal and varying from light to dark salmon pink as in "A." Same coloring on front and reverse sides of all petals. Type "C"—Predominantly white, with scattered "brush-stroke" streaks of salmon pink as in "A."
*Texture.*—Soft.
*Appearance.*—Satiny.
Fragrance: None.
Lasting quality: Excellent, on plant and as a cut flower.

*Genital Organs*

Stamens:
*Number.*—137.
*Length.*—1½ inches.
*Arrangement.*—One complete circle of stamens in center of bloom and composed of connected fascicles.
Pollen color: Yellow.

*Fruit*

Shape: Normal.
Fertile: Yes.
Color at maturity: Green.

The outstanding and distinctive character of my new camellia plant resides mainly in the fact that a single plant produces several different types of coloration in its blooms, thereby providing different color types of flowers, all growing on the same plant, and affording an attractive and interesting display which occurs again and again throughout the blooming season. The general color appearing in the blooms is pink, which varies from light to dark over different parts of the petals.

Having now disclosed my new variety of camellia plant, I claim:

A new and distinct variety of camellia plant, substantially as shown and described, characterized particularly by its production of pink colored blooms which occur simultaneously in at least three distinct coloration types, including blooms having all petals solidly colored pink, blooms with all petals having an over-all pink striped effect on a pink tinted white background, and blooms having petals that are predominantly white with scattered pink stripes, said plant being further characterized by its long recurrent-blooming season, its rapid and vigorous growth habits, its hardiness in cold weather, and its ability to bloom perfectly throughout its normal blooming season in spite of mid-season freezes.

No references cited.